(12) United States Patent
Sun et al.

(10) Patent No.: US 7,462,470 B2
(45) Date of Patent: Dec. 9, 2008

(54) METHOD FOR THE PRODUCING VANILLIC ACID AND VANILLIN FROM WASTE RESIDUE OF RICE BRAN OIL BY FERMENTATION AND BIOTRANSFORMATION

(75) Inventors: Zhihao Sun, Wuxi (CN); Pu Zheng, Wuxi (CN); Xinfu Guo, Hangzhou (CN); Guanyu Lin, Hangzhou (CN); Hanghua Yin, Hangzhou (CN); Jun Wang, Hangzhou (CN); Yanbing Bai, Hangzhou (CN)

(73) Assignee: Zhejiang Hangzhou Xinfu Pharmaceutical Co., Ltd, Zhejiang (CN)

(*) Notice: Subject to any disclaimer, the term of this patent is extended or adjusted under 35 U.S.C. 154(b) by 345 days.

(21) Appl. No.: 11/340,845

(22) Filed: Jan. 27, 2006

(65) Prior Publication Data
US 2006/0292676 A1   Dec. 28, 2006

(30) Foreign Application Priority Data
Jun. 17, 2005   (CN)   .................. 2005 1 0077191

(51) Int. Cl.
*C12P 7/24*   (2006.01)
*C12P 7/42*   (2006.01)

(52) U.S. Cl. .................. 435/146; 435/136; 435/147; 435/254.1; 435/254.3

(58) Field of Classification Search .................. 435/146, 435/147, 254.1, 254.3
See application file for complete search history.

(56) References Cited

U.S. PATENT DOCUMENTS 5,866,380 A * 2/1999 Lesage-Meessen et al. . 435/146

OTHER PUBLICATIONS

Stentelaire et al.; Design of a Fungal Bioprocess for Vanillin Production from Vanillic Acid at Scalable Level by *Pycnoporus cinnabarinus*; Journal of Bioscience and Bioengineering; vol. 89, No. 3, 223-230; 2000.
In the May 2000 edition of "Chemistry in Britain", pp. 48-50; Chemistry in Britain, 2000; 36 (5).

* cited by examiner

*Primary Examiner*—Herbert J. Lilling
(74) *Attorney, Agent, or Firm*—Browdy and Neimark, P.L.L.C.

(57) ABSTRACT

A method for the production of vanillic acid and vanillin from waste residue (niger) of rice bran oil by microbial fermentation and biotransformation is provided. The method of the present invention comprises the steps of hydrolization of ferulic acid esters in waste residue of rice bran oil to ferulic acid and further conversion into vanillic acid using microbial strain *Aspergillus niger* CGMCC 0774 screened and preserved by the present inventor, followed by conversion of vanillic acid to produce vanillin using another microbial strain *Pycnoporus cinnabarinus* CGMCC 1115. The method for the production of vanillin according to the present invention utilizes renewable source from rice processing and alleviates the environmental pollution caused by the chemical synthesis of vanillin.

5 Claims, 1 Drawing Sheet

METHOD FOR THE PRODUCING VANILLIC ACID AND VANILLIN FROM WASTE RESIDUE OF RICE BRAN OIL BY FERMENTATION AND BIOTRANSFORMATION

FIELD OF THE INVENTION

The present invention relates to a method for the producing vanillic acid and vanillin, and more particularly, to a method for the production of vanillic acid and vanillin from waste residue (niger, black oil) of rice bran oil by microbial fermentation and biotransformation.

BACKGROUND OF THE INVENTION

Vanilla aldehyde (4-hydroxy-3-methoxy-benzaldehyde), commonly referred to as vanillin, is the main fragrance ingredient of *Vanilla planifolia Andreurs* (Vanilla) which is prestigious as "the king of food-flavorings in the world". Vanillin possesses a pure perfume of vanilla pods as well as an intense taste of sweet, creamy and cocoa characteristics and salubrious scent. Therefore, vanillin is an important broadspectrum top-grade flavoring in the world and widely used in foodstuff, beverage, tobacco, alcoholic, cosmetic, pharmaceutical and chemical industries.

At present, "artifical" or semi-synthetical vanillins are mostly derived from benzene-based petrochemical materials. For example, vanillin may be synthesized from guaiacol through Reimer-Tiemann reaction or chemically synthesized from lignin as starting material. Although these methods are simple and can be used for the large-scale production of cheap products, these methods have a disadvantage of causing environmental pollution. In addition, the starting materials employed in these methods such as guaiacol is toxic. Extraction from plant (vanilla pods) is another production method for vanillin. Such a method, however, is limited by climate and terrain conditions and the production yield is low (about 20 ton per year), resulting in a high price (1,200-4,000 $/kg). Along with an increased emphasis on the food safety by society, the consumers' demand for natural flavorings in foods has increased over the years. The legal definition of "natural flavor" in both the US and the major European countries includes products obtained by fermentation and enzymatic processes (EC (88/388) and FDA (CFR21)). This definition offers the flavor industry the chance of using biotechnology for the production of natural flavors. To meet the people's need for natural vanillin, methods for the production of vanillin using microbes or enzymes have been developed. In the May 2000 edition of "Chemistry in Britain", pages 48-50, it is suggested that bio-conversion of ferulic acid to vanillin by liquid cultures of various fungi may be an economical route as well.

Ferulic acid, chemically similar to vanillin, is an important substrate for the whole transformation process from glucose to vanillin in plant, and therefore is considered as a promising precursor for vanillin. Gross et al. (U.S. Pat. No. 5,262,315) provides a process for producing vanillin by bioconversion of benzenoid precursors (the group consisting of vanillic acid and ferulic acid) by a basidiomycete fungus of the genus *Pycnoporus*, discloses that 0.3 g/L of ferulic acid is converted into 0.045 g/L of vanillin by *P. cinnabarinus* CNCMnDEG I-937 or CNCMnDEG I-938 with a molar conversion yield of 20.5%, wherein vanillic acid is transformed into vanillin with a conversion yield of 35.1%. Lesage-Meessen et al. (U.S. Pat. Nos. 5,866,380; 6,162,637) employs a two-step method using filamentous fungi to produce vanillin with an increased yield. The first step of the two-step method is to add ferulic acid to fermentation broth of microbial strain *Asp. niger* MIC 373, wherein ferulic acid is added in continuous fashion in the proportion of 430 mg/l per 24 hours to a final concentration of 5.05 g/L. After culturing for 15 days, the final concentration of vanillic acid in the culture is detected by HPLC to be 3.60 g/L. The added ferulic acids are consumed completely, wherein most of them (82%) are converted into vanillic acid, a minor part (2%) is metabolized into methoxyl hydroquinone and no vanillin or vanillin alcohol is produced. Alternatively, the fermentation broth of *Streptomyces setonii* strain ATCC 25497 is used to transform 0.88 g/L of ferulic acid into 0.332 g/L of vanillic acid after 100 hours of growth of the culture. The second step of the two-step method is to add vanillic acid to fermentation broth of microbial strain *Phanerochaete chrysosporium* MIC 247, wherein 0.3 g/L of vanillic acid is added sequentially (namely: 0.3 g/l at the end of 3 days of culture, then 0.3 g/l every day), and sterile resin XAD2 (Amberlite) is added in the proportion of 10% (weight/volume) after 3 days+6 h of culture of the fungus (that is to say 6 h after adding vanillic acid). Finally, 1.2 g/L of vanillic acid is reduced to 0.628 g/L of vanillin. The subsequent laboratory scale-up study on fermentor employs *P. cinnabarinus* MUCL 39533 in the conversion of vanillic acid into vanillin and the concentration of vanillin can reach 1,575 mg/L (Stenielaire C., Lesage-meessen. L., Oddou J. et.al., J of Biosci and Bioengineering. 2000, 89, 223-230). The above method employs two kinds of microbes in the conversion of ferulic acid (precursor) into vanillin, wherein the culturing of two kinds of microbes, the conversion reactions of two substrates and extraction of intermediate products (vanillic acid) are involved. Therefore, the whole production process is long and the production yield is low. Rabenhorst et al. (U.S. Pat. No. 6,133,003) discloses the cultivation of *Amycolatopsis* sp. DSM 9992, wherein ferulic acid is added to the culture in a stepwise manner. After 47 hours of culture, 7,317 ppm of vanillin is produced and 1,526 ppm of ferulic acid is left. This is a conversion rate of approximately 72% of theory. Muheim et al. (U.S. Pat. No. 6,235,507) discloses the cultivation of *S. setonii* ATCC 39116, wherein 5-40 g/L of ferulic acid is added to the culture in a stepwise manner when the carbon source (glucose) is almost exhausted after 5-40 hours of culture. The culture (biotransformation) is continued for about 5-50 hours and the accumulated vanillin from ferulic acid amounts to 8-16 g/L. A variety of byproducts such as vanillin alcohol, vanillic acid, guaiacol, p-ethenyl guaiacol and 2-methyl-4-ethylphenol, however, are produced in the above biotransformation, which results in a difficulty in separating and extracting converted product.

In the above-described methods for the production of vanillin from ferulic acid by microbial biotransformation, the sources of substrates employed (ferulic acid and vanillic acid) are not described in detail.

Natural ferulic acid exists in a form of trans-ferulic acid and is a constituent of cell wall of plant. Ferulic acid in the cell wall of rice bran plant mainly exists in a form of arabinose glycoside in waste residue of rice bran of plant cell wall. In addition, ferulic acid also exists in forms of cycloartanol and sterol ferulic acid esters in rice bran crude oil with a content of about 2-3%. The niger obtained after extraction of salad oil from rice bran crude oil is rich in ferulic acid esters with a content of about 70%, wherein ferulic acid amounts to up to 25-30% of the ferulic acid esters.

SUMMARY OF THE INVENTION

An objective of the invention is to provide an effective production method of vanillic acid and vanillin by microbial fermentation and biotransformation of natural starting materials. The inventive method adopts the hydrolyte of waste residue rice bran oil by microorganism as fermentation material directly, wherein the main constituents of the rice bran oil are cycloartanol and sterol ferulic acid esters. Alternatively, the waste residue rice bran oil may be used to produce ferulic acid or a solution containing ferulic acid, which is further used as starting material for the production of vanillic acid and vanillin by microbial transformation. In one embodiment, natural vanillin is produced by successive conversions with two kinds of microbes. In a preferred embodiment, Asp. niger CGMCC 0774 or a mutant thereof is used to hydrolyze waste residue oil to produce ferulic acid and further transform the ferulic acid into vanillic acid. The fermentation liquid containing vanillic acid is subjected to membrane treatment to remove microbial mycelium. Then cultured P. cinnabarinus CGMCC 1115 or a mutant thereof is added into the vanillic acid enriched culture to perform a reductive conversion reaction. For the purpose of eliminating the toxic effect of vanillin (product) on cells and enzymes, a water/organic solvent two-phase biocatalytic reaction system is adopted during the conversion, or alternatively an adsorptive resin is added. The product of biotransformation is extracted into the organic solvent or absorbed into the resin. After elution with ethanol, the product is concentrated, crystallized, and recrystallized to obtain vanillin with high purity.

Rice is abundant in China and its byproduct, rice bran, commonly amounts to 5-8% of rice. Therefore, the resource of rice bran is abundant in China with an annual yield of more than 1,0000,000 tons. A series of chemicals having healthcare function have been extracted from rice bran, for example functional oils and fats, oryzanol, γ-oryzanol, phytin, phytic acid, inositol, VB, VE etc. These functional ingredients have antineoplastic, hypoglycemic, hypolipidemic, hypocholesteremic, bactericidal, antiphologistic and immunity improving functions, respectively. The cost of starting materials to produce ferulic acid can be reduced by comprehensive utilization of rice bran.

The method of the present invention employs microbes to produce vanillin from natural material. The reaction condition is mild and the product is safe and environmentally benign with low content of harmful substance. In addition, the method of the invention is not changed by plant production and can be used for large-scale production with a short production cycle. Because rice bran, a renewable agriculture source, is used in place of benzene-based petrochemical materials derived from coal tar, the problems of scarcity of petrochemical resource and environmental pollution involved in the process of chemically synthesizing vanillin can be alleviated. Therefore, the method of the present invention is favorable for the development of society.

The present invention provides a method for the production of vanillic acid and vanillin comprising:

(1) culturing Aspergillus niger CGMCC 0774 in a fermentor;

(2) adding waste residue of rice bran oil containing ferulic acid to the fermentation broth of step (1) to obtain a converted liquid containing vanillic acid;

(3) filtrating the converted liquid of step (2) with a membrane, and autoclaving after supplementation with glucose;

(4) culturing Pycnoporus cinnabarinus CGMCC 1115 or a mutant thereof in a fermentor to obtain wet mycelium;

(5) mixing the wet mycelium of step (4) with the converted liquid of step (3) to perform a conversion reaction to produce a solution of vanillin;

(6) extracting vanillin from the solution of vanillin of step (5).

DETAILED DESCRIPTION OF THE INVENTION

In particularly, the invention provides a method for the production of vanillic acid and vanillin comprising:

(1) culturing Aspergillus niger CGMCC 0774 in a fermentor for 30-50 hours;

(2) adding waste residue of rice bran oil containing ferulic acid to the fermentation broth of step (1) in one-step or stepwise manner to obtain a final concentration of 1-15 g/L for ferulic acid, wherein the ferulic acid is converted for 24-80 hours and a converted liquid containing vanillic acid is obtained;

(3) filtrating the converted liquid of step (2) with a membrane to remove the mycelium formed, after which the converted liquid is adjusted to pH 4-6 and supplemented with 1-10 g/L of glucose, and then autoclaving;

(4) culturing Pycnoporus cinnabarinus CGMCC 1115 or a mutant thereof in a fermentor for 24-72 hours to obtain wet mycelium;

(5) mixing the wet mycelium of step (4) with the converted liquid of step (3) in a proportion of 10% (w/v) to perform a conversion reaction, wherein the reaction is continued for 24-80 hours and a solution of vanillin is obtained; and (6) extracting vanillin from the solution of vanillin of step (5).

In a preferred embodiment of above methods, 2-20% (w/v) of macroporous resin with a pore size of 80-200 Å or 20-80% (w/v) of organic solvent is added during the conversion reaction of step (5). Preferably, the macroporous resin is selected from the group consisted of HZ802, D001, D001-CC, D061, D113, DA201, HPD600, HPD300, and HPD100A (purchased from Shanghai Hua Zhen Technology and Trade Co. Ltd) and the organic solvent is selected from the group consisted of n-butyl acetate and dibutyl phthalate.

The present invention will be described in details hereinafter.

The present invention discloses a production method of vanillic acid and vanillin by microbial fermentation and biotransformation of natural starting materials. The above-described microbes Asp. niger CGMCC 0774 and P. cinnabarinus CGMCC 1115 have been deposited with China General Microbiological Culture Collection Center (CGMCC), Institute of Microbiology, Chinese Academy of Sciences, 13 Beiyitiao Zhongguancun, Beijing 100080, P. R. China, under the terms of the Budapest Treaty on Jul. 19, 2002 and Mar. 17, 2004, respectively.

The method according to present invention involves the following steps:

(1) Preparation of Natural Ferulic Acid or an Aqueous Solution Containing the Same Slant culture of Asp. niger CGMCC 0774: a culture medium containing 1% to 10% of glucose, 5% to 30% of potato extract and 1% to 2.5% of agar is formulated, pH 6-9. All of the contents of constituents are percentage of weight to volume, i.e. g/100 ml (similarly hereinafter). The culture medium is autoclaved at 120° C. for 20-50 minutes and made into slants after cooling. The strain Asp. niger CGMCC 0774 is inoculated on the slants and incubated at 20-40° C. for 3-7 days.

Seed culture and fermentation: a culture medium containing 5-50 g/L of maltose, 0.2-10 g/L of diammonium tartrate, 1-5 g/L of yeast extract, 0.2-2 g/L of potassium dihydrogen phosphate, 1-10 g/L of calcium chloride and 0.2-5 g/L of magnesium sulfate is formulated, pH 4-9. Then 20 to 150 ml of the culture medium is added to a 250 ml flask and autoclaved at 100-120° C. for 20-50 minutes. The strain *Asp. niger* CGMCC 0774 is inoculated into the culture medium in an amount of 5% to 10%. The shake-flask fermentation is performed at 20-40° C., 100-250 rpm for 1-5 days. The resulted cultures are used as seed and fermentation culture, respectively.

Enzymatic hydrolysis of ferulic acid esters: a solution of niger of rice bran oil is added to the above cultured fermentor broth of *Asp. niger* CGMCC 0774 and hydrolysis reaction is conducted at 25-40° C. for 24-48 hours. Thereafter the formed mycelium is removed by filtration with 0.2 µm filter membrane. After addition of n-hexane for extraction of sterols, the culture medium is acidified to pH 4-5 by addition of diluted acid. A precipitation of ferulic acid is collected by filtration with 0.2 µm filter membrane and adjusted to pH 7.0 by addition of 10% NaOH to obtain a solution of ferulic acid, which can be used directly for the microbial biotransformation. The concentration of ferulic acid is detected by HPLC method (Li, Sun et.al., Simultaneous determination of ferulic acid, vanillic acid and vanillin by RP-HPLC, *Chinese Journal of Analytical Chemistry*, 2004, 32 (3): 409.). Alternatively, the above solution of ferulic acid may be used to prepare finished product of ferulic acid by conventional crystallization process.

(2) Preparation and Treatment of Vanillic Acid Converted Liquid

Under the seed culture and fermentation conditions described above, the seed of *Asp. niger* CGMCC 0774 is inoculated into fermentor and cultured at 30-37° C., 100-200 rpm with an aeration of 0.5-1 vvm. The substrate, ferulic acid obtained as above, is added to the fermentor broth to a final concentration of 1-4 g/L when the pH of fermentor broth decreases to a value below pH 3.5, and the conversion reaction is performed for 30-54 hours. 1-4 g/L of ferulic acid (substrate) is supplemented to the broth and the incubation is continued until the ferulic acid is nearly exhausted. The formed mycelium is removed by filtration with 0.2 µm filter membrane and pH is adjusted to pH 4-5. After supplementation of 0.2-5 g/L of glucose, the culture medium is autoclaved at 100-120° C. for 20-50 minutes. A solution containing 1-3 g/L of vanillic acid is obtained after cooling. The molar conversion yield of ferulic acid to vanillic acid is 64% to 86%.

*Aspergillus niger* CGMCC 0774 obtained by screening possesses not only the activity of ferulic acid esterase, but also the capability of oxidation cleavage of side chain of ferulic acid. Therefore, the hydrolysis of ferulic acid esters and the further conversion of ferulic acid into vanillic acid can be performed in one step. Because *Aspergillus niger* lacks the ability of reduction of to vanillin, *P. cinnabarnus* CGMCC 1115 is employed to convert vanillic acid to the desired product, vanillin.

(3) Preparation of Vanillin by Biotransformation

Slant culture of *P. cinnabarnus* CGMCC 1115: a culture medium containing 1% to 10% of glucose, 5% to 30% of potato extract and 1% to 2.5% of agar is formulated, pH 6-9. The culture medium is autoclaved at 100-120° C. for 20-50 minutes and made into slants after cooling. The strain *P. cinnabarnus* CGMCC 1115 is inoculated on the slants and incubated at 20-40° C. for 3-7 days.

Seed culture and fermentation: a culture medium containing 0.1-30 g/L of glucose, 0.1-15 g/L of beef broth, 0.1-10 g/L of yeast extract, 0.1-2.0 g/L of potassium dihydrogen phosphate, 0.1-0.5 g/L of magnesium sulfate and 0.1-1.0 g/L of calcium chloride is formulated, pH 3-8. Then 20 to 150 ml of the culture medium is added to a 250 ml flask and autoclaved at 100-120° C. for 20-50 minutes. The strain *P. cinnabarnus* CGMCC 1115 is inoculated into the culture medium in an amount of 5% to 10%. The shake-flask fermentation is performed at 20-35° C., 100-250 rpm for 36-72 hours. The resulted cultures are used as seed and fermentation culture, respectively. *Aspergillus niger* CGMCC 0774 was cultured for 36-48 hours under fermentor conditions at 20-40° C., 50-100 rpm with an aeration of 0.5-1 vvm. Mycelium is obtained by centrifugation or filtration and can be directly used for the biotransformation of vanillic acid.

The obtained mycelium is inoculated into the sterilized vanillic acid converted liquid of above (2) in an amount of 10% and conversion reaction is performed under fermentor conditions at 20-40° C., 50-100 rpm with an aeration of 0.2-0.8 vvm. During the reaction, 20-80% (w/v) of organic solvent such as n-butyl acetate and dibutyl phthalate, or alternatively 2-20% (w/v) of macroporous resin with a pore size of 80-200 Å is added to the culture medium, wherein the macroporous resin is selected from the group consisted of HZ802, D001, D001-CC, D061, D113, DA201, HPD600, HPD300, and HPD100A (D001: Shanghai Resin Factory Co. Ltd; D001-CC/D061: The Chemical Plant of NanKai University; HZ802、DA201 D113: Shanghai Hua Zhen Technology and Trade Co. Ltd; HPD-100A、HPD300、HPD600: Cangzhou Bon Chemical Co., LTD). The conversion reaction is performed for 24-80 hours and the continuously produced vanillin is extracted into the organic solvent or absorbed into the resin. The reaction is stopped when the concentration of resin in the culture medium is close to zero. The final concentration of vanillin can reach 1.8-4.0 g/L and the molar conversion yield of vanillic acid to vanillin can be up to 60-80%.

(4) Extraction of Vanillin

The organic solvent or the absorptive resin is separated from the reaction solution and eluted with 100% ethanol to obtain an organic phase enriched in vanillin. The organic phase is subjected to dehydration by saturated sodium chloride solution and concentrated in vacuum at 30-70° C. The solvent is recovered to obtain a concentrated solution of 100-600 g/L vanillin. After cooling and agitating the concentrated solution, crude crystal of vanillin with a purity of 70% to 80% is obtained. The crude crystals is redissolved into ethanol-water (0.01-0.8, v/v) solution and heated to 60-85° C. After the complete dissolution of crude crystal of vanillin, the solution is cooled to 0-10° C. and stands for crystallization. The crystal obtained by filtration to remove mother liquor is washed with cold ethanol and dried in vacuum at 50° C. Finally, ivorywhite or light brown crystal of vanillin with a purity of 99% is obtained.

The following are outstanding features of the invention.

(1) Rice bran, an agricultural byproduct, is employed as the starting material of ferulic acid to produce natural vanillin (i.e. bio-vanillin) by biotransformation. The method according to the present invention utilizes renewable source from rice processing in place of benzene-based petrochemical materials derived from coal tar and is safe for the food production. In addition, the method of the invention can be used to solve the problems of scarcity of petrochemical resource and environmental pollution involved in the process of chemically synthesizing vanillin. The inventive method also decreases the production cost of vanillin remarkably.

(2) A reaction-separation couple technique is adopted in the above biotransformation. The technique solves the problem of product inhibition satisfactorily and in particular eliminates the toxic effect of vanillin on cells and enzymes (the product of biotransformation is up to 1.8-4.0 g/L). The technique also facilitates the separation of product and reduces the production cost as well as energy consumption.

(3) The method of the invention realizes the successive conversions from ferulic acid to vanillic acid and then to vanillin by using two kinds of microbes. Compared with two-step production process, the method according to the present invention reduces the production process as well as production cycle significantly and improves the production yield of vanillin.

Figure 1:
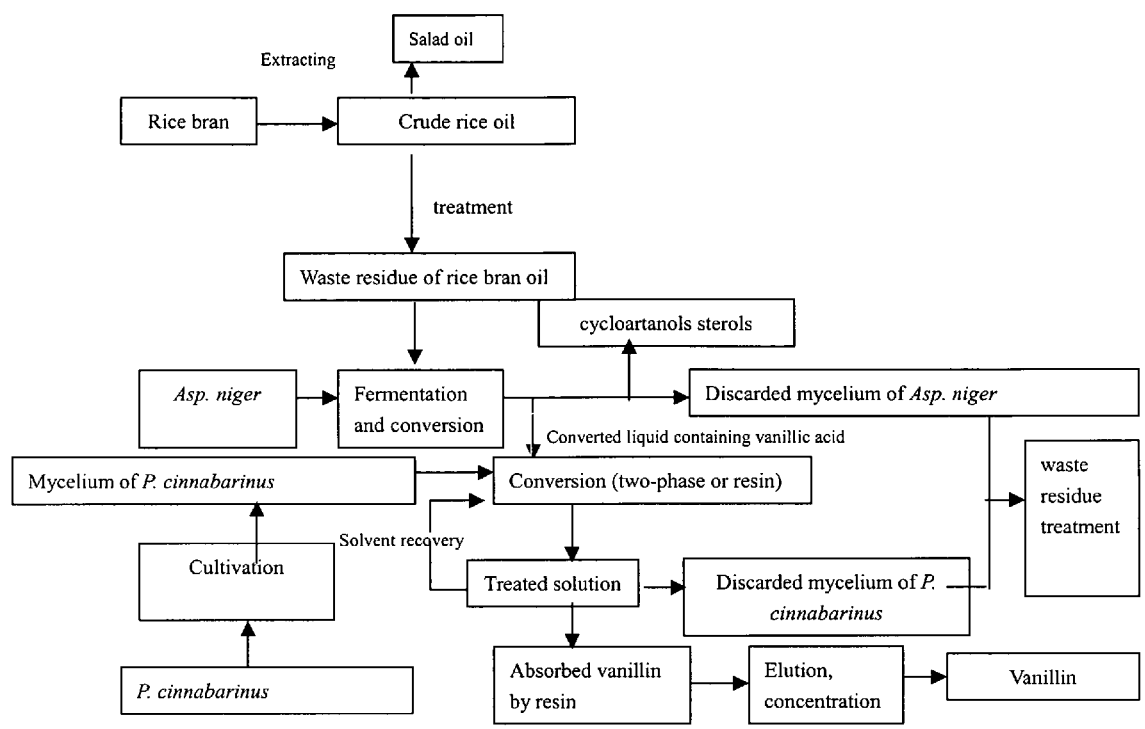
FIG. 1 is a process flow diagram of method according to the present invention.

In order to more fully demonstrate the advantages arising from the present invention, the flowing examples are set forth. It is to be understood that the following is by way of example only and is not intended as a limitation on the scope of the invention.

EXAMPLE

Example 1

A mycelial mass was scraped from a grown fresh slant of *Asp. niger* CGMCC 0774 and added to 100 mL of sterilized water. Glass beads were added to the water and beating was continued at 180 rpm for 20 minutes. The concentration of spore solution obtained was about $10^6$/mL. The spore solution was inoculated into 800 mL of seed culture medium in an amount of 10% and incubated at 30° C., 170 rpm for 2 days. The seed culture was shattered for 20 minutes and the solution obtained was added to a fermentation medium, which had been autoclaved at 120° C. for 20-50 minutes and cooled. The fermentation medium contained 20 g/L of maltose, 10 g/L of diammonium tartrate, 2 g/L of yeast extract, 1 g/L of potassium dihydrogen phosphate, 5 g/L of calcium chloride and 0.5 g/L of magnesium sulfate, pH 7.0. The fermentation conditions were as follows: 100 ml culture medium/250 ml flask, seed volume: 10%, 35° C., 120 rpm. After culture for 40 hours, a solution of niger of rice bran oil was added to the culture medium in a proportion of 10 g/100 ml of culture. The concentration of ferulic acid in the culture was 2.02 g/100 ml. The hydrolysis by fermentation was performed at 37° C. for 24 hours. An HPLC analysis was carried out to detect the concentrations of ferulic acid and vanillic acid. The final concentrations of ferulic acid and vanillic acid were 1.22 g/100 ml and 0.68 g/100 ml, respectively.

Example 2

*Asp. niger* CGMCC 0774 was cultivated according to Example 1. The seed culture was placed in an inoculation bottle, inoculated into a 15 L fermentor filled with 8 L sterilized fermentation broth and cultured for 44 hours under fermentor conditions at 37° C., 200 rpm, with an aeration of 1 vvm and 0.1 Mpa of tank pressure. 1 L of 10 g/L sterilized ferulic acid solution (sodium salt solution, pH 7.0) obtained in Example 1 was added and conversion reaction was performed under the same conditions for 34 hours. Sampled at constant time interval and detected by Thin-Layer Chromatography (TLC). Upon the ferulic acid was nearly exhausted, the concentration of vanillic acid was detected to be 0.506 g/L, corresponding to a molar conversion yield of 83.32%. The biomass (thallus dry weight) could reach up to 4.8 g/L.

Example 3

*Asp. niger* CGMCC 0774 was cultivated according to Example 1. The strain was inoculated into 1.6 L of seed culture medium in an amount of 10% and cultured at 30° C., 170 rpm for 2 days. The seed culture was placed in an inoculation bottle, inoculated into a 25 L fermentor filled with 16 L sterilized fermentation broth and cultured for 41 hours under fermentor conditions at 37° C., 200 rpm, with an aeration of 1 vvm and 0.1 Mpa of tank pressure. When pH decreased to a value below pH 3.1, 1 L of 36 g/L sterilized ferulic acid solution (sodium salt solution, pH 7.0) obtained by concentration or crystallization in Example 1 was added and conversion reaction was performed under the same fermentor conditions for 36 hours, wherein the concentration of ferulic acid in converted liquid was detected to be 2.0 g/L. Thereafter, 33 g ferulic acid was formulated into 1L sterilized solution of ferulic acid sodium salt (pH 7.0) and fed to the culture medium. The concentration of ferulic acid in converted liquid was detected to be 2.3 g/L. The conversion reaction continued for 72 hours. HPLC analysis was carried out to detect the substrate and product of conversion. The concentration of ferulic acid was 2.24 g/L, corresponding to a molar conversion yield of 64.6%.

Example 4

A seed culture (48 h) of *P. cinnabarinus* CGMCC 1115 was inoculated into fermentation medium in an amount of 10%. The fermentation medium contained glucose (20 g/L), beef broth (10 g/L), yeast extract (10 g/L), potassium dihydrogen phosphate (1 g/L), magnesium sulfate (0.5 g/L), calcium chloride (0.1 g/L) with an initial pH of 7.0. Then 100 ml of the culture medium is added to a 250 ml flask and cultured at 30° C., 120 rpm for 48 hours. Thereafter, 1 g/L, 2 g/L, 3 g/L, 4 g/L or 5 g/L of vanillic acid was added to the culture media, respectively. 12 hours later, Resin HZ802 was added and conversion continued with shaking. After 48 hours, HPLC analysis was carried out and the results were shown in Table 1. As seen from Table 1, the concentration of vanillin reached 2.197 g/L with a molar conversion yield of 60.69% when the concentration of substrate (vanillic acid) was 4 g/L, and reached 2.498 g/L with a molar conversion yield of 55% when the concentration of the substrate was 5 g/L and 25 g resin was used. The production of vanillin was further increased to 2.787 g/L with a molar conversion yield of 61.59% by extension of the conversion time to 72 hours.

TABLE 1

The productions of vanillin under different concentrations of substrate after conversion for 48 h

|  | Maximal Concentration (g/L) | Molar conversion yield | Residual vanillic acid (g/L) |
|---|---|---|---|
| 1 g/L + 5 g resin | 0.474 | 52.37 | 0.002 |
| 2 g/L + 10 g resin | 1.286 | 71.05 | 0.202 |
| 3 g/L + 15 g resin | 1.746 | 64.31 | 0.381 |
| 4 g/L + 20 g resin | 2.197 | 60.69 | 0.678 |
| 5 g/L + 25 g resin | 2.498 | 55.20 | 1.601 |

Example 5

*P. cinnabarinus* CGMCC 1115 was cultivated according to Example 4. The strain was inoculated into a 25 L fermentor filled with 16 L sterilized fermentation broth in an amount of 10% and cultured for 48 hours under fermentor conditions at 30° C., 100 rpm, with an aeration of 1:1 vvm and 0.1 Mpa of tank pressure. When pH decreased to the minimum value (pH 2.9), ferulic acid solution was added to obtain a final concentration of 2 g/L. The temperature was elevated to 35° C. and the aeration decreased to 0.3 vvm. After 12 hours, 10% (w/v) of HZ802 was added and conversion reaction was performed for 57 hours. The concentration of vanillin reached the maximal value, 1.446 g/L, corresponding to a molar conversion yield of 79.9%.

Example 6

Seed culture of *Aspergillus niger* CGMCC 0774 (2 days) was inoculated into fermentation medium. After cultivating for 2 days, a solution of niger of rice bran oil containing cycloartanol and sterol ferulic acid esters as main ingredients was added (the concentration of ferulic acid: 4 g/L), and the fermentation was kept on at 37° C., 150 rpm for 2 days. A converted liquid containing 1.960 g/L of vanillic acid and 0.897 g/L of residual ferulic acid was obtained. The converted liquid was adjusted to pH 5.0 and supplemented with glucose to a final concentration of 5.0 g/L. After sterilization, the converted liquid was inoculated with mycelium of *P. cinnabarinus* CGMCC 1115 cultured (48 h) according to Example 4 in an amount of 10% to perform conversion reaction. During the conversion, resin HZ802 was added. After conversion for 50 hours, the concentration of vanillin reached the maximal value, 1.066 g/L, corresponding to a molar conversion yield of 60.1% over vinillic acid and a molar conversion yield of 34.01% over ferulic acid.

Example 7

*P. cinnabarinus* CGMCC 1115 was cultured according to the process of Example 5. 1 g of mycelium of *P. cinnabarinus* cultured for 48 h was inoculated into 100 mL of converted liquid containing 3.98 g/L vanillic acid and 5 g/L glucose (pH 4.5) to carry out the conversion. 100 mL of each solvent shown in Table 2 was added to the reaction to form a water/organic solvent two-phase bioreaction system, respectively. The bioconversion was performed at 35° C., 180 rpm with shaking. The continuously produced vanillin was extracted into the organic solvent. After 24 hours, the reaction was stopped and the experimental results were shown in Table 2.

TABLE 2

The effect of organic solvent on the conversion of vanillic acid to vanillin by *P. cinnabarnus* CGMCC1115

| Orgainc solvents | Vanillin (mg)/100 mL organic solvent |
|---|---|
| n-hexane | 10.8 |
| cyclonexane | 8.1 |
| n-heptane | 6.2 |
| n-octane | 6.4 |
| isopropyl ether | 2.5 |
| methyl tert-butyl ether | 112 |
| carbon tetrachloride | 0 |
| dibutyl phthalate | 250 |
| n-butyl acetate | 158 |
| isobutanol | 15.0 |
| n-hexyl alcohol | 18.1 |
| Control (no solvent added) | 102 mg/100 mLwater |

Example 8

The conversion reaction was carried out in 25 L fermentor according to Example 6. 299 g resin absorbing vanillin was taken out, dipped in and eluted with 95% ethanol. 1860 ml of eluent was collected and the concentration of vanillin therein was detected by HPLC to be 1.865 g/L. After concentration in vacuum at 50° C., the volume of solution was reduced to about 170 ml and the concentrated solution contained 2.60 g vanillin. The concentrate was extracted with ethyl acetate for three times, dried over saturated sodium chloride and anhydrous magnesium sulfate solution, and finally 480 ml ethyl acetate solution containing 5.474 g/L vanillin was obtained. The acquired ethyl acetate solution was concentrated in vacuum into a sticky liquid and yellow brown crystal powdered vanillin was gradually produced. After drying at 35° C., 2.89 g crude crystal of vanillin was obtained and the purity of crystal was detected by HPLC to be 77%. 12 volumes of hot ethanol-water (ethanol:water=0.1:1 (v/v)) at 85° C. was added to 1.89 g of crude crystal and pH was adjusted to 7.0. After cooling, precipitated brown oil was removed. After cooling again, crystal precipitated was filtered and dried. The content of vanillin in the obtained light brown crystal was detected by HPLC to be 95%. Recrystallization was repeated twice to obtain 0.87 g ivorywhite crystal. The purity of final crystal was detected by HPLC to be 99.01%.

What is claimed is:
1. A method for the producing vanillic acid and vanillin comprising:
 (1) culturing *Aspergillus niger* CGMCC 0774 in a fermentor;
 (2) adding waste residue of rice bran oil containing ferulic acid to the fermentation broth of step (1) to obtain a converted liquid containing vanillic acid;
 (3) filtrating the converted liquid of step (2) with a membrane, and autoclaving after supplementation with glucose;
 (4) culturing *Pycnoporus cinnabarinus* CGMCC 1115 or a mutant thereof in a fermentor to obtain wet mycelium;
 (5) mixing the wet mycelium of step (4) with the converted liquid of step (3) to perform a conversion reaction to produce a solution of vanillin; and
 (6) extracting vanillin from the solution of vanillin of step (5).

2. A method for the production of vanillic acid and vanillin comprising:
 (1) culturing *Aspergillus niger* CGMCC 0774 in a fermentor for 30-50 hours;
 (2) adding waste residue of rice bran oil containing ferulic acid to the fermentation broth of step (1) in one-step or stepwise manner to obtain a final concentration of 1-15 g/L for ferulic acid, wherein the ferulic acid is converted for 24-80 hours and a converted liquid containing vanillic acid is obtained;
 (3) filtrating the converted liquid of step (2) with a membrane to remove the mycelium formed, after which the converted liquid is adjusted to pH 4-6 and supplemented with 1-10 g/L of glucose, and then autoclaving;
 (4) culturing *Pycnoporus cinnabarinus* CGMCC 1115 or a mutant thereof in a fermentor for 24-72 hours to obtain wet mycelium;
 (5) mixing the wet mycelium of step (4) with the converted liquid of step (3) in a proportion of 10% (w/v) to perform a conversion reaction, wherein the reaction is continued for 24-80 hours and a solution of vanillin is obtained; and
 (6) extracting vanillin from the solution of vanillin of step (5).

3. The method according to claim 1 wherein 2-20% (w/v) of macroporous resin with a pore size of 80-200 Å or 20-80% (w/v) of organic solvent is added during the conversion reaction of step (5).

4. The method according to claim 3, wherein the macroporous resin is selected from the group consisting of styrene adsorption resins, strong acidic cation exchange resins, acrylic acid cationic resin, styrene anionic resin, polar adsorption resins and non-polar adsorption resins.

5. The method according to claim 3, wherein the organic solvent is selected from the group consisted of n-butyl acetate and dibutyl phthalate.

* * * * *